United States Patent [19]
Wong-Staal et al.

[11] Patent Number: 5,650,309
[45] Date of Patent: Jul. 22, 1997

[54] VIRAL VECTORS

[75] Inventors: Flossie Wong-Staal, San Diego; Michael Mamounas, Solana Beach; Eric M. Poeschla, San Diego; Gunter Kraus; Mark Leavitt, both of La Jolla, all of Calif.

[73] Assignee: The Regents of the University of California, Oakland, Calif.

[21] Appl. No.: 442,061

[22] Filed: May 16, 1995

[51] Int. Cl.$^6$ ..................................................... C12N 15/63
[52] U.S. Cl. ............................ 435/172.3; 435/320.1; 435/240.2; 536/24.5; 536/24.1; 536/23.1
[58] Field of Search .................. 435/320.1, 172.3, 435/240.2, 235.1, 91.4, 235, 91.32, 91.1, 91.3, 240.1; 536/27, 23.2, 24.1, 24.5, 23.1; 935/22, 57, 32; 424/199.1, 93.2

[56] References Cited

U.S. PATENT DOCUMENTS 5,474,935 12/1995 Chatterjee et al. ................. 435/320.1

OTHER PUBLICATIONS

Chatterjee et al., *Science* (1992) 258: 1485–1488.
Chatterjee and Wong, *Methods, A Companion to Methods in Enzymology* (1993) 5: 51–59.
Yu. et al., *Gene Therapy* (1994) 1: 13–26.
Baltimore, *Nature* (1988) 335: 395.
Marcus–Sekura, *Analytical Biochemistry* (1988) 172: 289–295.
Samulski et al., *J. Virol.* (1987) 61(10): 3096–3101.
Ojwang et al., *Proc. Nat'l Acad. Sci. USA*, (1992) 89: 10802–06.
Weintraub, *Sci. Am*, (Jan. 1990) 262: 40–46.
Haseloff, et al., *Nature* (1988) 334: 585–591.
Richardson, J.H. et al. *J. of virol.* 1993 pp. 3997–4005.
Barinaga, M. 1994 *Science* 266: pp. 1326.
Marshall, E. 1995 *Science* 269: 1050–1055.
Crystal, R.G. 1995 *Science* 270: 404–410.

*Primary Examiner*—James Ketter
*Assistant Examiner*—Irem Yucel
*Attorney, Agent, or Firm*—Townsend and Townsend and Crew LLP

[57] ABSTRACT

Vectors are provided which stably transduce cells, rendering the cells resistant to a target virus. The vectors are amplified upon infection of the cell by a target virus, and spread throughout an infected host in response to infection by the target virus.

21 Claims, 8 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: RNA     ( i x ) FEATURE:
        ( A ) NAME/KEY: misc_feature
        ( B ) LOCATION: 1..40
        ( D ) OTHER INFORMATION: /note= "Tar sequence"

( x i ) SEQUENCE DESCRIPTION: SEQ ID NO:1:

UCUUAGGCUC UGAUGAGUCC GUGAGGACGA AGACUUCCUG     40

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear     ( i i ) MOLECULE TYPE: DNA     ( i x ) FEATURE:
        ( A ) NAME/KEY: misc_feature (B) LOCATION: 1..18
(D) OTHER INFORMATION: /note= "Hammerhead ribozyme"

(x i) SEQUENCE DESCRIPTION: SEQ ID NO:2:

CAGGAAGTCA GCCTAAGA                                                                                             1 8

VIRAL VECTORS

This invention was made partially with government support under NIH grant 5-R01-AI29889, awarded by the National Institutes of Health. The United States Government has certain rights in this invention.

BACKGROUND OF THE INVENTION

Cells can be stably transduced with a number of viral vectors including retroviruses and adeno-associated viruses. Retrovirus-based vectors are useful due to their ability to transduce cells efficiently with target nucleic acids, and because of their ability to integrate a target nucleic acid into a cellular genome.

Adeno-associated viral ("AAV") vectors are also used to transduce cells with target nucleic acids, e.g., those which inhibit deleterious gene function. AAV is replication defective, requiring co-infection with a helper virus such as adenovirus for productive infection. However, AAV vectors efficiently transduce many different cell types, including hematopoietic cells. Cells transduced with AAV vectors do not have to be actively dividing as in the case of retroviral vectors.

AAV vectors have no endogenous promoter activity, permitting expression of desired recombinant sequences within the AAV vector from engineered promoters. AAV vectors are used to inhibit, e.g., viral infection, by including anti-viral transcription cassettes in the AAV vector. For example, Chatterjee et al. (*Science* (1992), 258: 1485–1488, hereinafter Chatterjee et al. 1) describe anti-sense inhibition of HIV-1 infectivity in target cells using an AAV vector with a constitutive expression cassette expressing anti-TAR RNA. Chatterjee et al. (PCT application PCT/US91/03440 (1991), hereinafter Chatterjee et al. 2) describe AAV vectors, including AAV-vectors which express antisense TAR sequences. Chatterjee and Wong (*Methods, A companion to Methods in Enzymology* (1993), 5: 51–59) further describe AAV vectors for the delivery of antisense RNA.

AAV vectors have several properties which make them preferred gene delivery systems. They have no known mode of pathogenesis and 80% of people in the United States are currently seropositive for AAV. Because AAV vectors have no endogenous promoter activity, specific promoters may be used, depending on target cell type. Packaged AAV vectors can be concentrated so that multiplicities of infection exceeding 1.0 can be used in transduction experiments. This allows virtually 100% of the targets in a culture to be transduced, obviating the need for selection of transduced cells.

This invention provides composite viral vectors with elements for host chromosome integration derived from one virus and a replication-defective rescuable viral genome which includes an anti-viral agent derived from another virus. The anti-viral agent is generally directed against the virus corresponding to the replication-defective portion of the vector. Cells transduced by this construct block infection by wild-type versions of the replication-defective virus. Moreover, if the infecting virus successfully replicates within the transduced cell, the replication-defective portion of the vector (including the anti-viral agent) will also replicate, causing the anti-viral activity contained within the replication-defective construct to spread throughout an infected host, in parallel with the viral infection. Thus, the construct provides protection against infection by a particular virus, and the protection is amplified upon infection by the virus.

SUMMARY OF THE INVENTION

The present invention provides vectors constructed to afford two levels of anti-viral activity once they are transduced into a biological host cell. The first level of anti-viral activity is provided by an anti-viral agent encoded by the vector which is transduced into a host cell. The secondary protective effect is produced upon infection of the host cell by a target virus, which causes the nucleic acid encoding the anti-viral agent to be replicated and encapsidated into viral particles, which then deliver the nucleic acid encoding the anti-viral agent to other cells within the host, thereby blocking or ameliorating infection by the target virus within the host.

The first part of the vector is derived from a biologically cis-active nucleic acid encoding sequences which facilitate incorporation of the vector into a host cell chromosome. Many such sequences are known, including various transposons and viral integration elements such as the HIV LTR and AAV ITR. The second part of the vector encodes a replication defective, rescuable viral genome. The genome is rendered replication defective by deleting or inactivating a portion of the vector which encodes an element (e.g., a nucleic acid or protein) necessary for viral replication, or is itself necessary for viral replication. The second part of the vector also includes a nucleic acid which encodes an anti-viral agent, or viral inhibitor, such as a ribozyme, anti-sense nucleic acid, decoy gene, transdominant gene or suicide gene. The anti-viral agent is operably linked to an expression control sequence such as a promoter, e.g., a constitutive promoter, or an inducible promoter, e.g., a promoter activated by a viral protein.

In one class of preferred embodiments, this anti-viral agent, or inhibitor, is directed against viruses which correspond to the replication defective portion of the vector, such that viral replication of invading replication competent viruses corresponding to the replication defective portion of the virus is inhibited by the anti-viral agent. In a second class of preferred embodiments, the target virus is a virus other than that corresponding to the replication defective portion of the vector. For instance, in one embodiment, the replication defective portion of the vector is derived from a retrovirus, while the anti-viral agent is directed against a DNA virus. For instance, in one embodiment, the replication defective portion of the vector is engineered such that an element of the virus is placed under the control of a transcription factor encoded by a second unrelated virus.

Where the replication defective portion of the virus is derived from an HIV virus, the replication defective, rescuable HIV genome would be rendered replication defective by modifying the HIV promoter region (e.g., the HIV LTR), or by deleting or modifying a gene or genes whose product is necessary for viral replication, such as a gene encoding a protein necessary for transcription of the virus or a viral structural protein, including the tat, rev, gag, pol, env, vif, vpr, nef, and vpu/vpx genes. In preferred embodiments, more than one gene is deleted or altered, rendering the replication defective portion of the genome less likely to revert to an infective phenotype upon mutation. For instance, when the replication defective portion of the genome is derived from HIV, a preferred embodiment has 3 or 4 defective or missing genes, e.g., selected from the group tat, rev, gag, pol, env, v/f, vpr, nef, and vpu/vpx.

In one class of embodiments, the anti-viral agent is a nucleic acid encoding a viral inhibitor such as an antisense nucleic acid comprising the HIV TAR or RRE sequence, a decoy nucleic acid molecule comprising the TAR sequence or the RRE sequence, or a hammerhead or hairpin ribozyme directed against the HIV 3' leader sequence.

The present invention also provides for cells (e.g., mammalian cells) transduced with the vector described above. Useful cells include cultures of in vitro cells resistant to contamination by a target virus of the vector, as well as ex vivo and in vivo cells which provide resistance to an organism against a target virus. These cells include hematopoietic stem cells, fetal cord blood cells, T-lymphocytes and monocytes. In one class of embodiments, these cells provide factors which permit replication of the replication defective portion of the virus. For instance, in vitro cell lines for the production of replication-defective viral particles corresponding to the replication-defective portion of the vector can be established. These replication-defective viral particles are non-infectious (reducing the risk of unwanted pathogenicity) and can be used as antigens, e.g., in diagnostic assays to determine whether an individual is infected with the corresponding replication-competent virus.

The present invention provides methods for inhibiting viral replication in a cell, comprising transducing the cell with the vector described above. These methods confer resistance to any target virus which is inhibited by the anti-viral agent encoded by the vector, including, e.g., HIV, HTLV and HBV. In one class of embodiments, the cell is transduced ex vivo with a vector of claim 1 and introducing the transduced cell into the individual. In another class of embodiments, the cell is transduced in vivo by administering the vector to the individual. The present invention also provides methods for making anti-viral agents in a cell in vitro, comprising transducing the cell in vitro with the vector described above, wherein the cell includes genes necessary for activating the expression control sequence which directs expression of the anti-viral agent, and culturing the cell under conditions for expression of the anti-viral agent.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa.

The term "biologically active nucleic acid sequence" refers to a nucleic acid which has the property of encoding or possessing a property which directs or permits an activity in a host cell. For instance, the nucleic acid optionally encodes proteins or catalytic nucleic acids which act upon the nucleic acid or the host cell upon transcription and/or translation and/or has sequences necessary for chromosomal integration into the host cell's genome, nucleic acid origins of replication, and sequences which permit packaging of the nucleic acid into a viral capsid.

The term "cis-active nucleic acid" refers to a nucleic acid subsequence which encodes or directs the biological activity of a nucleic acid sequence. For instance, cis-active nucleic acid includes nucleic acid subsequences necessary for chromosomal integration of a nucleic acid sequence into a host chromosome, nucleic acid subsequences which encode transcription factors which direct replication of the full-length nucleic acid sequence, nucleic acid subsequences which encode structural proteins necessary for encapsidation of the nucleic acid sequence and origins of nucleic acid replication.

The term "constitutive" promoter refers to a promoter which is active under most environmental and developmental conditions.

The term "encapsidation" generically refers to the process of incorporating a nucleic acid sequence (e.g., a vector, or a viral genome) into a viral particle. No distinction is made between the type of nucleic acid and the type of viral particle. Thus, encapsidation refers to the process of placing a nucleic acid sequence (e.g., single-stranded RNA, double-stranded RNA, single stranded DNA and double-stranded DNA) into any type of viral particle, i.e., "capsid" is a generic term used to indicate any type of viral shell, particle or coat, including a protein capsid, a lipid enveloped structure, a protein-nucleic acid capsid, or a combination thereof (e.g., a lipid-protein envelope surrounding a protein-nucleic acid capsid).

The term "host cell" or "target cell" refers to a cell transduced with a specified vector. The cell is optionally selected from in vitro cells such as those derived from cell culture, ex vivo cells, such as those derived from an organism, and in vivo cells, such as those in an organism.

The term "identical" in the context of two nucleic acid or polypeptide sequences refers to the residues in the two sequences which are the same when aligned for maximum correspondence. Optimal alignment of sequences for comparison can be conducted, e.g., by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

An "inducible" promoter is a promoter which is under environmental or developmental regulation.

The terms "isolated" or "biologically pure" refer to material which is substantially or essentially free from components which normally accompany it as found in its native state. The isolated nucleic acid vectors of this invention do not contain materials normally associated with their in situ environment, in particular nuclear, cytosolic or membrane associated proteins or nucleic acids other than those nucleic acids intended to comprise the nucleic acid vector itself.

The term "labeled nucleic acid probe" refers to a nucleic acid probe that is bound, either covalently, through a linker, or through ionic, van der Waals or hydrogen "bonds" to a label such that the presence of the probe may be detected by detecting the presence of the label bound to the probe.

The term "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin, dioxigenin, or haptens and proteins for which antisera or monoclonal antibodies are available.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means.

A "replication defective rescuable viral genome" is a nucleic acid which cannot package itself into a viral capsid and/or replicate itself in a host cell using components encoded by the nucleic acid. The nucleic acid is replicated and encapsidated upon infection by a target virus, or if it is transduced into a cell which supplies the functions necessary for encapsidation/replication in trans (i.e., supplies the functions which are missing or altered such that the nucleic acid cannot replicate itself in a typical host cell).

A "ribozyme sequence" is a catalytic RNA sequence capable of cleaving a target RNA, such as a hairpin or hammerhead ribozyme. The term also encompasses a nucleic acid sequence in an expression cassette from which the RNA is transcribed.

The term "subsequence" in the context of a particular nucleic acid sequence refers to a region of the nucleic acid equal to or smaller than the specified nucleic acid.

A "target virus" is a virus that supplies functions which allow the replication defective viral genome to replicate when it infects a cell transduced with the replication defective viral genome. Typically, the replication defective viral genome includes an anti-viral agent directed against the target virus.

The term "vector" refers to a composition for transferring a nucleic acid (or nucleic acids) to a host cell. A vector comprises a nucleic acid encoding the nucleic acid to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

DETAILED DESCRIPTION

This invention provides viral vectors which protect transduced cells from viral infection, and which expand the protective effect of the vector to other cells in a host upon viral infection. The vectors have elements for host cell chromosome integration and a replication-defective rescuable viral genome which includes an anti-viral agent. The anti-viral agent is generally directed against the virus corresponding to the replication-defective portion of the vector. Cells transduced by this construct block infection by wild-type versions of the replication-defective virus. Moreover, if anti-viral activity in any transduced cell fails, the vector is designed to include a secondary protective function. If the infecting virus successfully replicates within the transduced cell, the replication-defective portion of the vector (including the anti-viral agent) will also replicate and "infect" other cells of the host in parallel with the infecting virus. Thus, the anti-viral activity contained within the replication-defective construct is spread throughout an infected host in parallel with the viral infection.

The vectors are useful for introducing anti-viral genes into cells, and for spreading the anti-viral genes to other cells within a host upon infection by a virus or a class of viruses. The vectors have a genome containing a cellular transduction portion and an anti-viral portion. The cellular transduction portion contains sequences for integrating the vector into a host chromosome, and optionally contains additional sequences, such as those necessary for packaging the vector into a virus particle. In preferred embodiments, the cellular transduction portion of the virus does not replicate itself efficiently, requiring co-infection of the cell by a helper virus, or expression by the cell of viral regulators or components for productive infection. Any wild-type or modified viral genome which can incorporate the anti-viral portion can be used. AAV vectors are particularly preferred because they are able to encapsidate reasonably large amounts of DNA; they can be harvested and used in high concentrations for infection; they have no endogenous promoter activity, and they have no known mode of pathogenesis.

The anti-viral portion of the vector contains a replication defective, rescuable viral genome. Examples of viruses suitable for constructing the anti-viral portion of the vector include retroviruses, particularly the Lentivirinae and the Oncovirinae such as HIV-1, HIV-2, and HTLV-1, HTLV-2. A general introduction to viruses is found in *Principles and Practice of Clinical Virology*, Third Edition, (1994) Zuckerman et al. (eds) John Wiley and Sons, Ltd., and the references cited therein, and *Fundamental Immunology*, Third Edition Paul (ed) Raven Press, N.Y. and the references cited therein.

The replication defective genome encodes sequences which permit it to be replicated and packaged upon infection by the corresponding replication competent virus. Thus, in a cell transduced by the vector, the replication defective virus is replicated upon infection by the corresponding replication-competent (e.g., wild-type) virus. In some embodiments, the replication-defective portion of the virus is constructed to trigger productive replication upon infection by a virus which is unrelated to the replication-defective virus. For instance, in one embodiment, the replication-defective portion of the vector is constructed to achieve productive replication upon exposure to a transcription factor supplied by a target (related or unrelated) virus. In general, the vectors of these embodiments are constructed to permit an infecting virus to supply an element necessary for the replication of the replication-defective portion of the virus.

The anti-viral portion of the vector also encodes an anti-viral agent, such as a nucleic acid or protein (e.g., a ribozyme, an anti-sense sequence, a suicide gene, or a decoy gene) which disrupts the life-cycle of the virus from which the replication defective virus is derived. This portion of the vector is under the control of an expression control sequence, e.g., a promoter. In this context, a "promoter" or an expression control sequence refers to an array of transcription factor binding sites. In one class of embodiments an expression control sequence refers to a contiguous nucleic acid region near the start site of translation. In another class of embodiments, an expression control sequence is not contiguous, and includes sequences distal from the start site of transcription. The expression control sequence can be constitutive (e.g., a polymerase III promoter) or inducible. In one configuration, the expression control sequence responds to the same transcription factors as the virus which corresponds to the replication defective portion of the vector.

Cells transduced with the vector of the invention are rendered resistant to infection by the virus which corresponds to the replication-defective portion of the vector. As described above, the anti-viral portion of the integrated vector expresses an anti-viral agent, either constitutively, or in response to environmental stimuli, such as viral infection. This anti-viral agent blocks successful replication of the infecting virus. If the anti-viral agent does not completely block replication of the infecting virus, the replication-defective anti-viral portion of the vector is replicated in concert with the infecting virus. The replication-defective virus containing the anti-viral portion of the vector then infects other cells in concert with the corresponding replication competent virus. Because the replication defective portion of the virus contains an anti-viral agent, the anti-viral agent also "infects" other cells in concert with the replication competent (e.g., virulent wild-type) virus. Thus, the anti-viral agent blocks or ameliorates infection by the replication-competent virus in subsequent infections.

Infections with high titres of virus are generally more likely to overcome the viral suppression conferred to a cell by the anti-viral agent than an infection with a low titre of virus. Thus, propagation of the anti-viral agent occurs when it is most necessary, i.e., during acute infection by a viral pathogen.

A. Making Vectors

The practice of this invention involves the construction of nucleic acid vectors and the expression of genes in transfected cells. Molecular cloning techniques to achieve these ends is known in the art. A wide variety of cloning and in vitro amplification methods suitable for the construction of retroviral vectors are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); *Current Protocols in Molecular Biology*, F.M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Oligonucleotide synthesis, useful in cloning or amplifying nucleic acids, is typically carried out on commercially available solid phase oligonucleotide synthesis machines (Needham-VanDevanter et al. (1984) *Nucleic Acids Res.* 12:6159–6168) or chemically synthesized using the solid phase phosphoramidite triester method described by Beaucage et. al. (Beaucage et. al. (1981) *Tetrahedron Letts.* 22 (20): 1859–1862.

Methods of transfecting and expressing genes in mammalian cells are known in the art. Transducing cells with viral vectors can involve, for example, incubating viruses with cells within the viral host range under conditions and concentrations necessary to cause infection. See, e.g., *Methods in Enzymology, vol.* 185, Academic Press, Inc., San Diego, Calif. (D.V. Goeddel, ed.) (1990) or M. Krieger, *Gene Transfer and Expression—A Laboratory Manual*, Stockton Press, New York, N.Y., (1990), incorporated herein by reference.

Typically, vectors are initially constructed as plasmids using standard cloning techniques. They are then amplified in an appropriate cell which permits the vector to be packaged into a virion. The host cell line, e.g., HeLa cells, is optionally infected with an appropriate helper virus (e.g., adenovirus in the case of an AAV vector) for amplifying the vector and producing vector particles (i.e., vector packaged into a virion). The host cell line then is co-transfected with the vector genome and any necessary helper plasmid/virus. Upon incubation, the cell line will produce the vector for harvest and subsequent use.

The culture of cells used in the present invention, including cell lines and cultured cells from tissue samples is well known in the art. Freshney (*Culture of Animal Cells, a Manual of Basic Technique, third edition* Wiley-Liss, New York (1994)) provides a general guide to the culture of cells.

B. In Vitro Utility

The vectors are useful for inhibiting replication of the virus corresponding to the replication deficient virus in a cell in vitro, ex vivo or in vivo. The vector inhibits infection and/or replication of the virus. Methods useful for inhibiting viral replication in vitro and ex vivo involve transducing a cell with a vector of this invention. The cells can be from an organism, e.g., a mammal, or from cell culture. Resulting cell lines which are resistant to cellular pathogens are commercially useful due to the reduced likelihood of contamination of the cells with a viral pathogen, e.g., HIV.

In some embodiments, the cells which are transduced constitutively express a portion of the vector, e.g., genes from the replication defective portion of the virus. These products are harvested for use in commercially valuable western immunoblot assays for the detection of antibodies to the gene products in an organism. The presence of antibodies in the organism is diagnostic for infection of the organism by the corresponding virus. For instance, various HIV gene products can be produced and used in immunoblot assays for the detection of antibodies to HIV in patients. Immunoblot assays are currently in common commercial use for the detection of virally-mediated diseases and viral infections, including HIV.

(i) Immunoassays

A variety of immunoassay formats may be used to detect antibodies specifically immunoreactive with a particular antigen. For example, solid-phase ELISA immunoassays are routinely used to select monoclonal antibodies specifically immunoreactive with a protein. See, e.g., Coligan (1991) *Current Protocols in Immunology* Wiley/Greene, N.Y.; and Harlow and Lane (1989) Antibodies: A Laboratory Manual Cold Spring Harbor Press, N.Y. Techniques for preparing antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495–497.

A particular antibody or antigen can be quantified by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays,"*Laboratory Techniques in Biochemistry and Molecular Biology*, Elsevier Science Publishers B.V., Amsterdam; Harlow and Lane, supra; Chan (ed.) (1987) *Immunoassay: A Practical Guide Academic Press*, Orlando, Fla; Price and Newman (eds.) (1991) *Principles and Practice of Immunoassays Stockton Press*, N.Y.; and Ngo (ed.) (1988) *Non isotopic Immunoassays Plenum Press*, N.Y.

Immunoassays generally utilize a labeling agent to specifically bind to and label the binding complex formed by the capture agent and the analyte. The labeling agent may itself be one of the moieties comprising the antibody/analyte complex. Thus, the labeling agent may be a labeled viral vector expression product or a labeled anti-viral vector product antibody. The labeling agent may also be a third moiety, such as another antibody, that specifically binds to the antibody/vector product complex, or to a modified capture group (e.g., biotin) which is covalently linked to the marker gene peptide or anti-marker gene antibody.

A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Use of labels is also described in Ausbel, Sambrook, and Harlow and Lane (all supra).

(ii) Infectivity Assays

The vectors of this invention can be used to determine whether virally infected cells have been infected with a particular virus. In one embodiment of this method, one group of the cells in a sample to be tested is transduced with a vector of this invention. Another group serves as a control. Both groups are incubated under conditions and for sufficient time for viral replication. After incubation, each group is examined for evidence of viral infection. Evidence of viral infection in the control group but not in the test group, indicates that cells in the test group are infected by a virus corresponding to the anti-viral portion of the vector.

C. Ex Vivo Therapy

Methods for inhibiting viral replication in a cell in an organism involve transducing the cell ex vivo with a vector of this invention, and introducing the cell into the organism. The cells can be, for example, hematopoietic stem cells, which are derived from bone marrow or fetal cord blood or T-lymphocytes or monocytes (e.g., cultured from a patient). Alternatively, the cells can be those stored in a cell bank (e.g., a blood bank). Because the vector will inhibit viral replication in any of those cells already infected with the virus corresponding to the replication deficient anti-viral portion of the vector, an organism infected with the virus can be treated for the infection by transducing a population of its cells with the vector of the invention and introducing the transduced cells back into the organism as described below.

In the past, most ex vivo strategies directed against viral diseases such as AIDS have relied upon isolating cells which are not infected with the virus causing the disease, and transfecting the cells with a related anti-viral virus construct to confer resistance to the virus. As a practical matter, transfecting cells which are already infected has been impractical because of viral interference between the infective virus and the construct in the infected cell. The present invention overcomes this difficulty by providing a viral coat for the anti-viral portion of the construct which, in a preferred embodiment, is unrelated to the anti-viral portion. For instance, viral interference could block transfection of an anti-HIV construct with an HIV coat into a cell which is already HIV infected. In a preferred embodiment of the present invention, this problem is overcome, e.g., by providing an AAV viral coat for the anti-HIV portion of the vector. Thus, the present invention provides a method of protecting cells in vitro, ex vivo or in vivo, even when the cells are already infected with the virus against which protection is sought.

D. In Vivo Therapy

The vector can be administered directly to the organism for transduction of cells in vivo. Administration can be by any of the routes normally used for introducing virus into ultimate contact with blood or tissue cells. The vectors of the present invention can be used to treat virally-mediated diseases such as AIDS in patients. The vectors used in the present inventive method are administered in any suitable manner, preferably with pharmaceutically acceptable carriers. Suitable methods of administering such vectors in the context of the present invention to a patient are available, and, although more than one route can be used to administer a particular vector, a particular route can often provide a more immediate and more effective reaction than another route.

Pharmaceutically acceptable carriers are determined in part by the particular vector being administered, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The vector, alone or in combination with other suitable components, can be made into aerosol formulations to be administered via inhalation. Because the bronchial passageways are the usual route of choice for certain viruses, corresponding vectors are appropriately administered by this method. Aerosol formulations can be placed into pressurized acceptable propellants, such as dichlorodifluoromethane, propane, nitrogen, and the like.

Suitable formulations for rectal administration include, for example, suppositories, which consist of the active vector with a suppository base. Suitable suppository bases include natural or synthetic triglycerides or paraffin hydrocarbons. In addition, it is also possible to use gelatin rectal capsules which consist of a combination of the vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. For many vectors, this mode of administration will not be appropriate, because many virions are destroyed by lyophilization. Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, since cells are destroyed by lyophilization.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector or transduced cell type in a particular patient.

In determining the effective amount of the vector to be administered in the treatment or prophylaxis of virally-mediated diseases such as AIDS, the physician needs to evaluate circulating plasma levels, vector toxicities, and progression of the disease.

In the practice of this invention, the vectors can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions.

The vectors of this invention can supplement treatment of vitally-mediated conditions by any known conventional therapy, including cytotoxic agents, nucleotide analogues and biologic response modifiers.

For administration, vectors and transduced cell types of the present invention can be administered at a rate determined by the LD-50 of the vector, and the side-effects of the vector or cell type at various concentrations, as applied to the mass and overall health of the patient. Administration can be accomplished via single or divided doses.

E. Anti-viral Agents

The vectors of this invention include at least one "anti-viral agent" or "viral inhibitor" operably linked to an expression control sequence. As used herein the terms "anti-viral agent" and "viral inhibitor" refer to any nucleic acid whose product, upon transcription or translation, inhibits the replication of a specified virus. Anti-viral agents are known in the art. The literature describes such genes and their use. See, for example, Yu et al., *Gene Therapy,* 1:13 (1994); Herskowitz, *Nature,* 329:212 (1987) and Baltimore, *Nature,* 335:395 (1988). Anti-viral agents useful in this invention include, without limitation, anti-sense genes, ribozymes, decoy genes, transdominant proteins and suicide genes.

i. Antisense genes

An antisense nucleic acid is a nucleic acid that, upon expression, hybridizes to a particular mRNA molecule, to a transcriptional promoter or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to viral gene transcripts. Two target sequences for antisense molecules are the first and second exons of the HIV genes tat and rev. Chatterjee and Wong, supra, and Marcus-Sekura (Analytical Biochemistry (1988) 172, 289–285) describe the use of anti-sense genes to block or modify gene expression.

ii. Ribozymes

A ribozyme is a catalytic RNA molecule that cleaves other RNA molecules having particular nucleic acid sequences. Ribozymes useful in this invention are those that cleave HIV gene transcripts. Ojwang et al., *Proc. Nat'l. Acad. Sci., U.S.A.,* 89:10802–06 (1992) provides an example of an HIV-1 pol-specific hairpin ribozyme. Wong-Staal et al. (U.S. Ser. No. 08/245,742) provide examples of hairpin and hammerhead ribozymes (e.g., those which cut at the sequence GUX). A hammerhead ribozyme directed against the sequence 5'- CAGGAAGTCA GCCTAAGA - 3' (Seq. ID No. 2) in the first exon of tar has the sequence: 5'- UCUUAGGCU [CUGAUGAGUC CGUGAGGACG AA]GACUUCCUG - 3' (Seq. ID No. 1).

iii. Decoy Nucleic Acids

A decoy nucleic acid is a nucleic acid having a sequence recognized by a regulatory nucleic acid binding protein (i.e., a transcription factor). Upon expression, the transcription factor binds to the decoy nucleic acid, rather than to its natural target in the genome. Useful decoy nucleic acid sequences include any sequence to which a viral transcription factor binds. For instance, the TAR sequence, to which the tat protein binds, and HIV RRE sequence, to which the rev proteins binds are suitable sequences to use as decoy nucleic acids.

iv. Transdominant Proteins

A transdominant protein is a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. In particular, rev can be made transdominant by eliminating the leucine-rich domain close to the C terminus which is essential for proper normal regulation of transcription. Tat transdominant proteins can be generated by mutations in the RNA binding/nuclear localization domain.

v. Suicide Genes

A suicide gene produces a product which is cytotoxic. In the vectors of the present invention a suicide gene is operably linked to an expression control sequence in the replication defective rescuable genome which is stimulated upon infection by the replication-competent form of the virus. Upon infection of the cell by competent virus, the suicide gene product is produced, thereby killing the cell and blocking replication of the virus.

Examples of antisense molecules, ribozymes and decoy nucleic acids and their use can be found in Weintraub, *Sci. Am.*, 262:40–46 (Jan. 1990); Marcus-Sekura, *Anal Biochem.*, 172:289–95 (1988); and Hasselhoff et al., *Nature*, 334:585–591 (1988), incorporated herein by reference.

F. AAV/HIV Vectors

For clarity, a series of specific embodiments are described below in detail, in which the replication-deficient anti-viral portion of the vector is derived from the human immunodeficiency virus (HIV) and the elements for vector replication and chromosomal integration are derived from AAV. One of skill will appreciate that other anti-viral components and replication/integration components can be constructed to prevent viral infection in transduced cells for any virally-mediated disease using similar strategies.

AAV is a single-stranded, replication-defective DNA virus with a 4.7 kb. genome. AAV has palindromic inverted terminal repeats (ITRs) responsible for site-specific integration into a host chromosome (e.g., the q arm of human chromosome 19). Molecular clones of the AAV genome are infectious following transfection into a helper-virus infected cell, facilitating genetic manipulation.

In one embodiment, the vector is an AAV/HIV chimeric vector. The AAV portion of the vector contains the sequences for incorporating the vector into a virion, and the AAV ITR sequences. The vector is produced at a high titer and is able to transduce a wide rage of host cells in vivo or in vitro. The HIV portion is replication defective and rescuable. It does not reproduce unless the cell is infected by active HIV, which complements any replication deficient elements. The anti-HIV agent is either constitutively expressed, or operably linked to the HIV LTR promoter, and expressed upon infection by active HIV, thereby suppressing infection by replication competent HIV viruses. If the suppression fails, the replication-defective HIV portion is transcribed, processed and encapsidated into an HIV virion. It then transfects other cells (e.g., CD4$^+$cells), conferring the anti-HIV gene to that cell.

For ready encapsidation into AAV, the genome is preferably between about 2 kb and about 4.7 kb. Therefore, the natural coding sequences of AAV can be removed and replaced with the HIV portion of the chimeric vector. The vector genome can also include a selectable marker, such as a gene conferring neomycin resistance to a transduced cell. The construction of an AAV-based vector with a neomycin resistance marker is described in R.J. Samulski et al., *J. Virol.*, 61:3096 (1987). In one embodiment of the invention, the AAV portion of the chimeric vector consists essentially of two ITRs of AAV. These sequences can be located at the 5' and 3' ends, respectively, of the chimeric vector.

The construction and manipulation of AAV-based vectors are known in the art. See, for example, Chatterjee and Wong (supra) and C.A. Muro-Cacho et al., *J. Immunol.*, 11:231 (1992).

In general, the replication defective rescuable HIV genome lacks at least one gene function required for replication of HIV which can be supplied by transcomplementation after it has integrated into the host chromosome. Genes which, when their function is lacking, render an HIV genome both replication defective and rescuable include regulatory genes, such as rev and tat; structural genes, such as gag, pol, and env. The accessory genes vif, vpr, nef and vpu/vpx can also be rendered defective, i.e., in combination with the deletion or mutation of the regulatory or structural genes.

Tat and rev encode proteins that act by binding to specific sequences in the HIV genome. Both functions can be supplied by trans-complementation upon infection with active HIV. Therefore, defects in these genes are suitable for rendering the HIV genome replication defective and rescuable. Similarly, structural genes supply proteins for viral encapsidation. They can be made defective in the vector genome and complemented by active HIV, genes transfected by another vector or genes supplied by the host cell. Vpr and vpu/vpx can also be supplied by trans-complementation.

A replication defective rescuable genome of this invention can contain multiple defective genes. For example, Looney and Wong-Staal describe multiple gene mutants of HIV (PCT/US93/12088). Genes rendered inactive are capable of trans-complementation in order to render the construct rescuable. Genes which are not necessary for packaging may also be partially or completely deleted.

Functions of HIV replication not supplied by trans-complementation which are necessary for replication of the replication-defective portion of the vector are present in the replication-defective rescuable portion of the vector. This includes, e.g., the TAR sequence, the sequences necessary for HIV packaging, the RRE sequence if the instability elements of the p17 gene of gag is included, and sequences encoding the polypurine tract.

Figure 1:
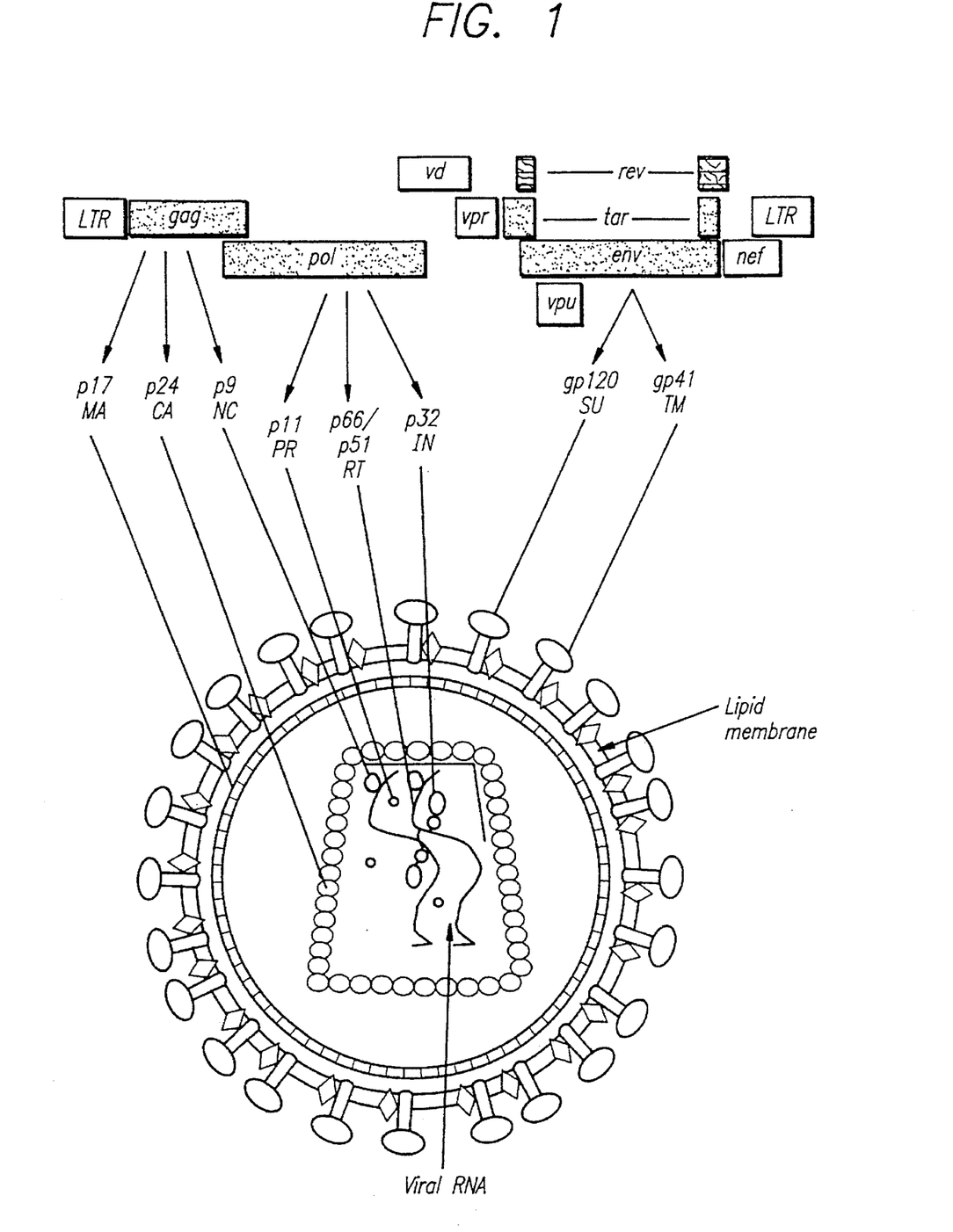
FIG. 1 depicts the structure of HIV.
Figure 2:
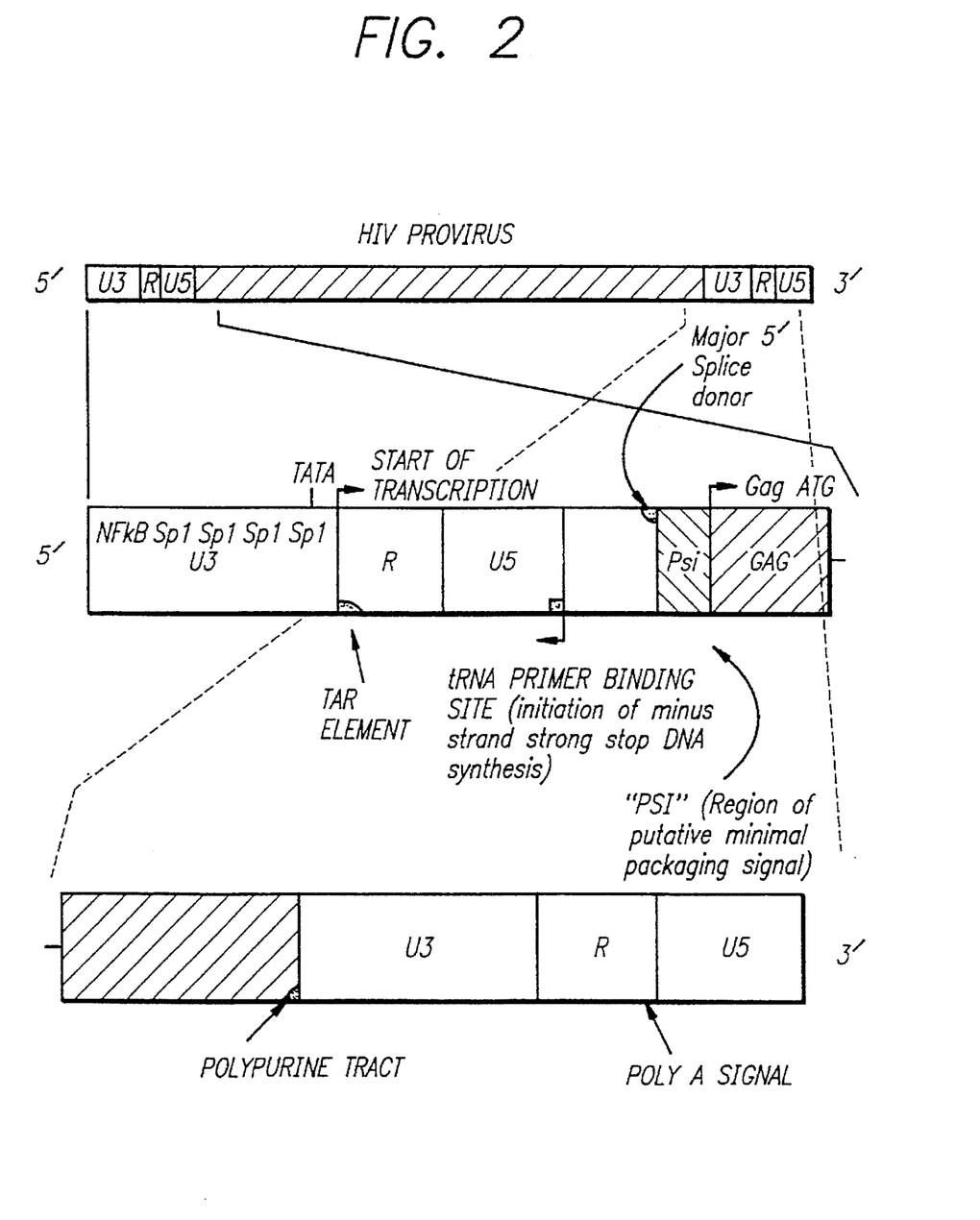
FIG. 2 is a map of the 5' and 3' portions of the HIV genome.

HIV sequences that contain these functions include a portion of the 5' long terminal repeat (LTR) and sequences downstream of the 5' LTR responsible for efficient packaging, i.e., through the major splice donor site ("MSD"), and the polypurine tract upstream of the 3' LTR through the U3R section of the 3' LTR. FIGS. 1 and 2 show the HIV genome and the location of relevant sequences.

The p17 gene contains INS (instability) elements that cause rapid degradation of the LTR promoter-mediated transcript in the absence of the Rev-RRE interaction. Therefore, if the INS sequences are included in the vector, the RRE is also included. However, if the HIV portion does not contain the INS sequence of p17, then the RRE sequence can be omitted. RRE is normally located in the envelope gene of HIV and is the sequence to which the rev protein binds.

The TAR sequence is located in the R portion of the 5' LTR. It is the sequence to which the tat protein binds.

The sequences necessary for packaging are located in the U5 portion of the 5' LTR and downstream of it into part of p17, as well as the U3R portion of the 3' LTR.

The polypurine tract is the sequence upstream from the 3' LTR site where RNAse H cleaves during plus ("+") strand DNA synthesis. It mediates plus strand synthesis.

The primate lentiviruses, including HIV 1, HIV 2 and SIV are structurally and functionally similar. Cognate portions of any of these viruses can be used in the vectors of the present invention in a manner similar to that described for HIV.

During transduction, the AAV/HIV chimeric vector integrates into the host chromosome, e.g., of T-cells and macrophage. Once introduced into an individual, these T cells and macrophage will be resistant to infection. Transduced hematopoietic stem cells will eventually differentiate into HIV target cells such as T cells and macrophage, which will also be resistant to infection by HIV.

Since both the AAV and HIV portions of the chimeric vector are replication defective, they will not spontaneously reproduce in any transduced cell. Where the anti-HIV gene is expressed constitutively, it will inhibit activity by any invading HIV. When the anti-HIV gene is operatively linked to the promoter in the 5' LTR, it will not normally be expressed if the tat gene is defective. However, upon infection of the cell by wild-type HIV, the invading virus expresses the tat protein, stimulating expression from the HIV LTR of the chimeric vector. In embodiments where the anti-viral agent is under the control of the HIV-LTR, this gene stimulation will produce the anti-HIV agent. Expression of the anti-HIV gene will incapacitate the invading virus, rendering it incapable of replication and subsequent infection.

If anti-viral activity in any cell fails, the chimeric vector is designed to include a secondary protective function. Although the HIV portion of the vector is replication defective, it is rescuable by active HIV virus. Factors produced by the infective HIV supplement the replication functions missing from the vector. Consequently, the transduced cell transcribes the replication-defective HIV portion, interfering with the packaging of wild type HIV, and/or subsequently disseminating the anti-HIV genes contained within the replication-defective HIV portion of the vector to other target cells.

Replication defective, rescuable HIV vectors are useful for introducing anti-HIV genes into cells and expressing those genes. The expression of anti-HIV genes in cultured cells is useful as a tool for understanding HIV function and can facilitate the evaluation of genes that inhibit HIV. Methods useful for expressing anti-HIV genes in a cell in vitro involve transducing a cell with a chimeric vector or replication defective, rescuable HIV vector of this invention, wherein the cell contains any genes necessary for activating the expression control sequence that is operatively linked to the anti-HIV gene, and culturing the cell under conditions for expression of the anti-HIV gene. Of course, when the anti-HIV gene is under the control of a constitutive promoter, no other genes are necessary for activation. When the anti-HIV gene is under the control of the HIV 5' LTR, then the activating gene can be introduced by infection with HIV, or by transfection with another vector carrying the tat gene. For example, if the anti-HIV gene is operatively linked to the HIV 5' LTR promoter, the cell should be made to express the tat gene.

EXAMPLES

The following examples are provided by way of illustration only and not by way of limitation. Those of skill will readily recognize a variety of noncritical parameters which can be changed or modified to yield essentially similar results.

Example 1

Construction of HIV-2 Based Retroviral Vector Plasmids and AAV Chimeric Vector Plasmids HIV-based retroviral vectors and AAV vectors were shown to transduce HeLa cells with an internal reporter construct. The HIV LTR was shown to drive expression of the reporter construct, and the HIV 3' polyadenylation site was shown to function in HeLa cells in the heterologous construct.

Figure 3:
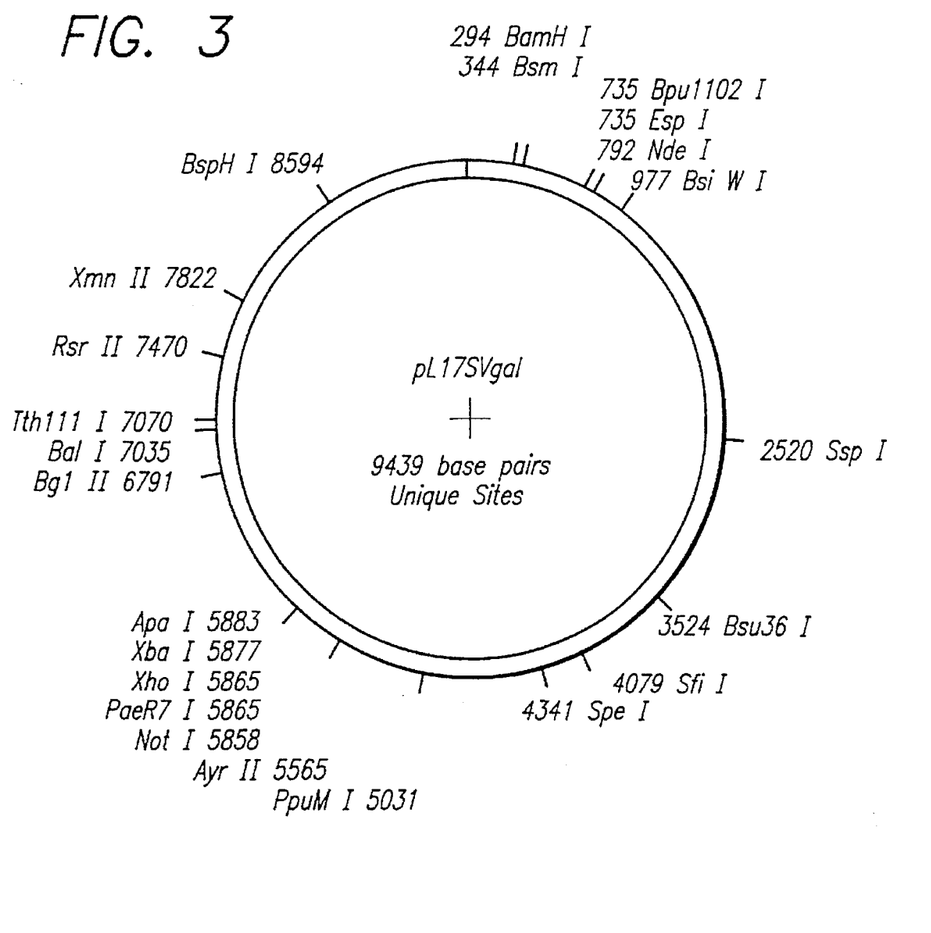
FIG. 3 depicts a circular map of plasmid pL17svgal.
Figure 4:
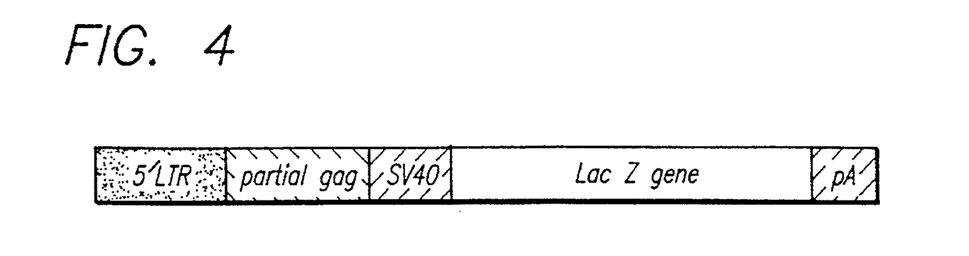
FIG. 4 depicts a linear map of plasmid pL17svgal.

A three-part ligation was performed to insert the HIV-2 KR LTR (Genbank No. U22047) and p17 portion of the gag gene upstream of a cassette containing the LacZ gene driven by the SV40 promoter. The lacz gene was excised from the plasmid pCH110. The resulting plasmid (pL17svgal) is illustrated in FIG. 3 as a circular DNA map and the vector portion of the plasmid is diagrammed in FIG. 4 as a linear map. Subsequent plasmids are similarly illustrated.

Transfection of this plasmid into HeLa cells produced strongly blue staining after fixation and standard X-gal staining, verifying the activity of the SV40-Lac Z expression cassette.

Figure 5:
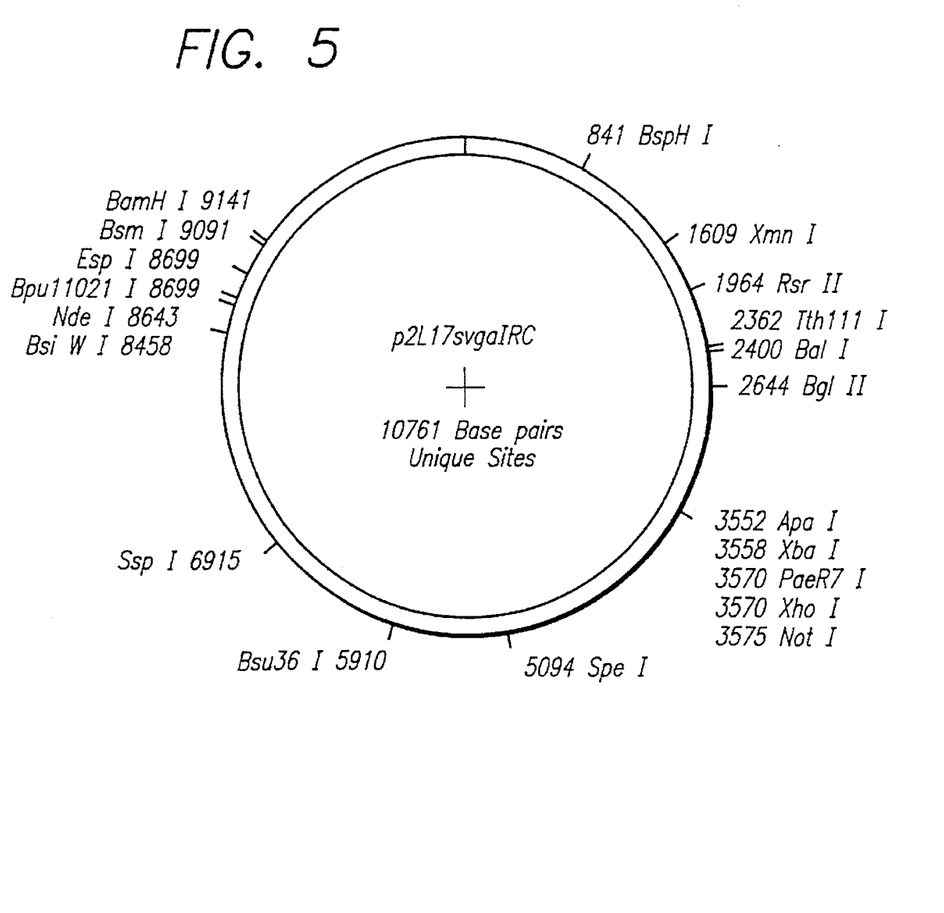
FIG. 5 depicts a circular map of plasmid p2L17svgal.
Figure 6:
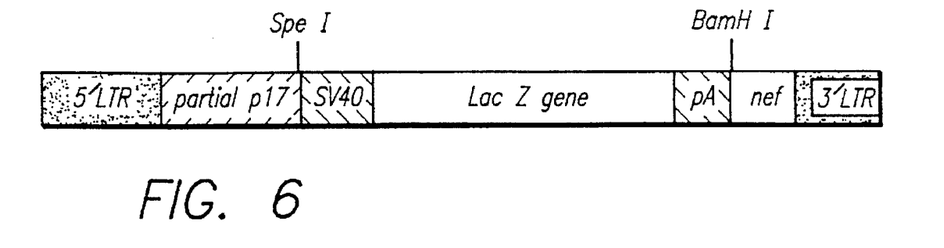
FIG. 6 depicts a linear map of plasmid p2L17svgal.

The 3' LTR was then inserted in pL17svgal to produce plasmid p2L17svgal, depicted in FIG. 5 and FIG. 6. This plasmid has two LTRs flanking an internal reporter gene (LacZ) driven by an internal promoter (SV40) and thus represents an initial retroviral vector construction. All but the first few amino acids of the nef gene open reading frame (beginning with the BamHI site) are also present, overlapping with the 3' LTR, as in the wild type HIV virus. This plasmid still has internal poly A signals.

Transfection of this plasmid directly into HeLA cells produced cells strongly positive by X-gal staining.

Next, in order to produce full length vector transcripts, the two internal poly A signals present at the end of the lacZ gene were deleted so that the first poly A signal encountered by pol II is the 3' LTR poly A signal. These signals were derived from the original pCH110 fragment which extended beyond the LacZ terminus of the plasmid. This deletion was accomplished by partial digest with DraI and full digest with BamH1. One of 5 DraI sites in p2L17svgal is present downstream of the Lac Z stop codon and upstream of the poly A signals. A unique BamHI site is located at the LacZ <->nef/LTR junction.

Figure 7:
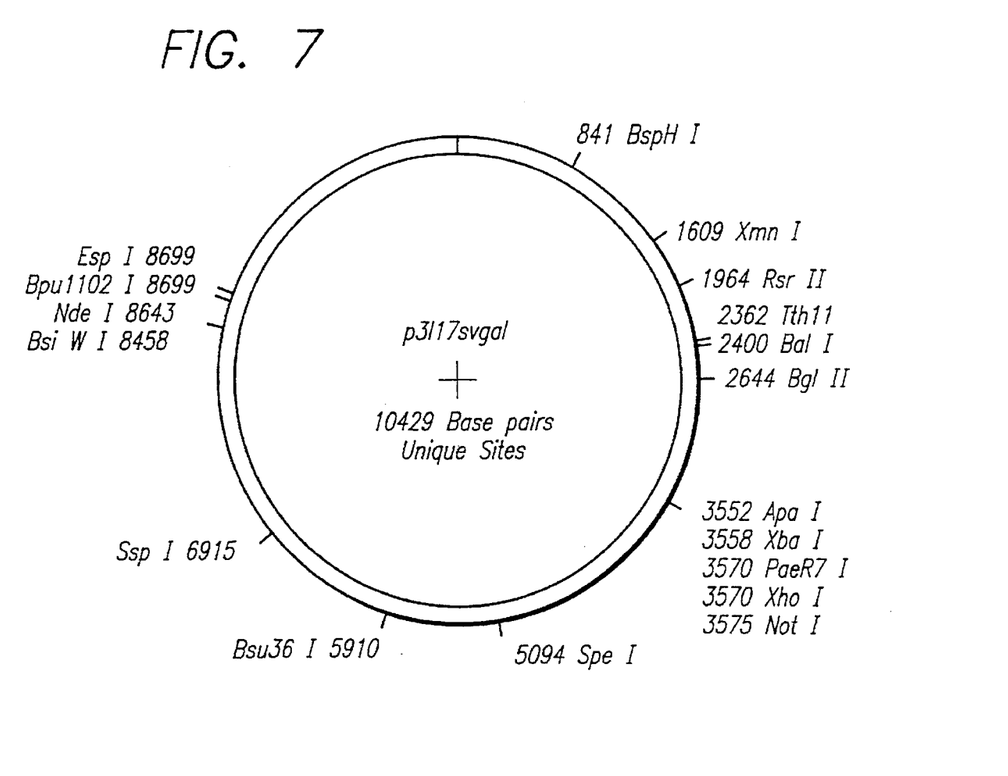
FIG. 7 depicts a circular map of plasmid p3L17svgal.
Figure 8:
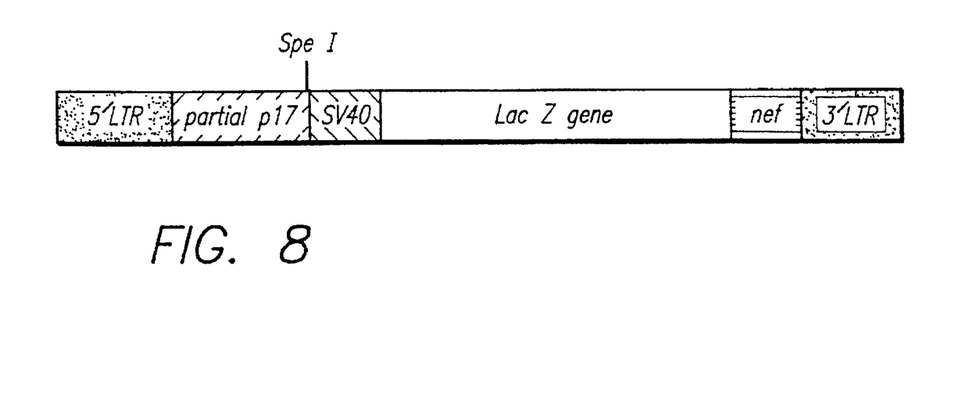
FIG. 8 depicts a linear map of plasmid p3L17svgal.

The singly cut DraI and BamHI fragment, having only the needed deletion was rescued by gel purification, blunted with Klenow fragment and ligated. This produced plasmid p3L17svgal, depicted in FIG. 7 and FIG. 8.

Transfection directly into HeLa cells produced strongly blue X-gal staining, indicating that translatable Lac Z transcripts were being expressed using the 3' LTR poly A signal.

A final modification was made by inserting either the HIV-1 or HIV-2 rev-response elements (RRE) into the speI site in order to render the full-length vector transcript protected by rev. This step was performed to prevent degradation of the transcript mediated through the p17 gag protein INS (instability) elements. The two resulting plasmids were named p3L17rrelsvgal and p3L17rre2svgal.

Transfection of p3L17rre2svgal with full-length HIV-1 molecular clones into HeLa cells, followed by filtration and passage of supernatant to HeLa-CD4 cells produced rare X-gal positive Hela-CD4 cells; this procedure demonstrated the transducibility of this vector, albeit at low efficiency.

Figure 9:
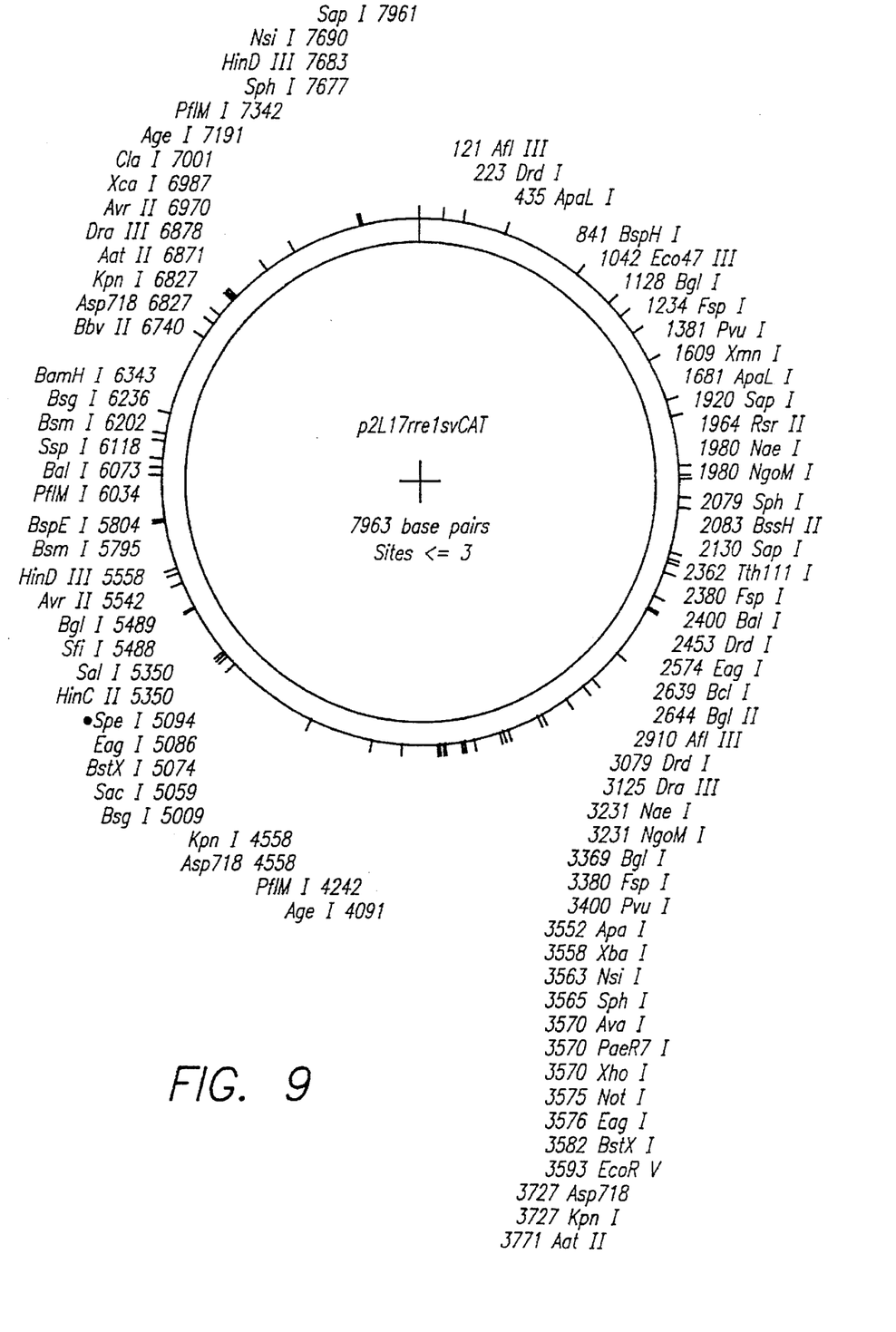
FIG. 9 depicts a circular map of plasmid p2L17rrelsvCAT.
Figure 10:
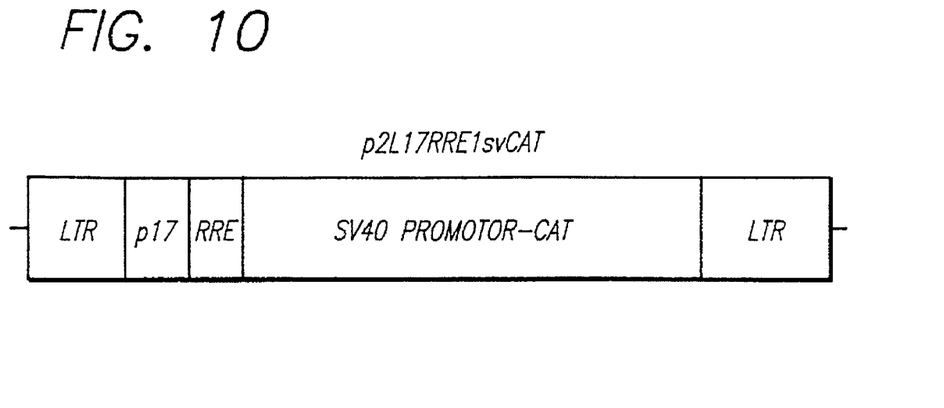
FIG. 10 depicts a linear map of plasmid p2L17rrelsvCAT.

Since the p3l17rre2svgal vector is 7 kilobases in size, it is too large to be inserted into an AAV vector (size limit about 4.7 kb). Therefore, the shorter chloramphenicol acetyltransferase (CAT) was substituted as the reporter gene. This was accomplished by a three part ligation utilizing a PCR-amplified RRE (from HIV-1 MN), a p2L17svgal BamH1-SpeI backbone fragment and a SalI-BamH1 sv40-CAT cassette from pSVCAT. The resulting plasmid was designated p2L17rrelsvCAT, depicted in FIG. 9 and FIG. 10.

Figure 11:
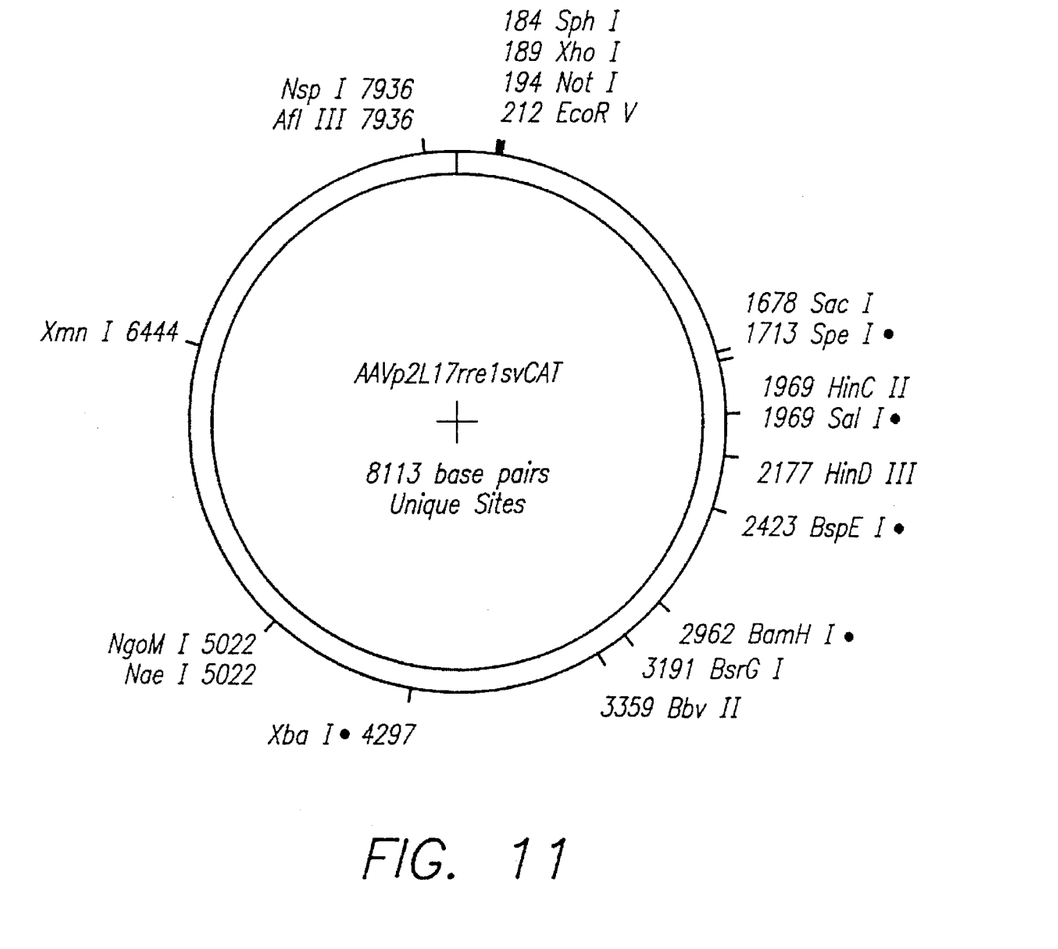
FIG. 11 depicts a circular map of plasmid AAVp2L17rrelsvCAT.
Figure 12:
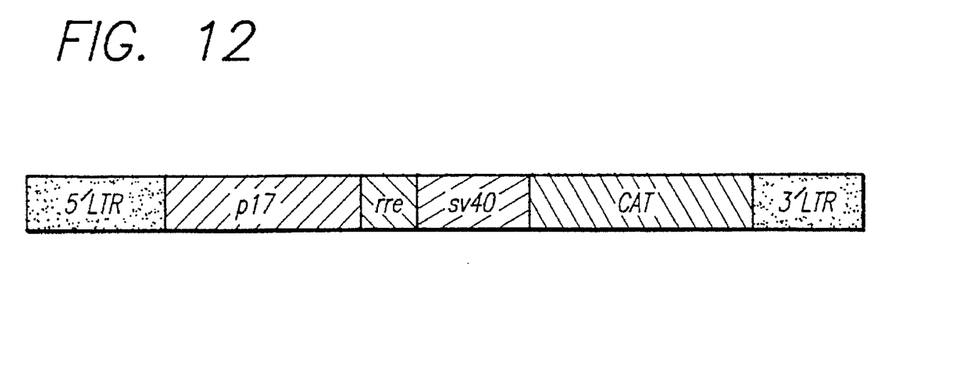
FIG. 12 depicts a linear map of plasmid AAVp2L17rrelsvCAT.

To insert the HIV-2 vector cassette from p2L17rrelsvcat into AAV, the former was digested with SphI, using the SphI sites flanking the HIV LTRs. Xba linkers were ligated and cut and the resulting Xba-linked fragment was cloned between the Xba sites of SSV9aav. This step placed the two ITRs of AAV just flanking the HIV-based CAT vector. The resulting plasmid was designated aavp2L17rrelsvCAT, depicted in FIG. 11 and FIG. 12.

Figure 13:
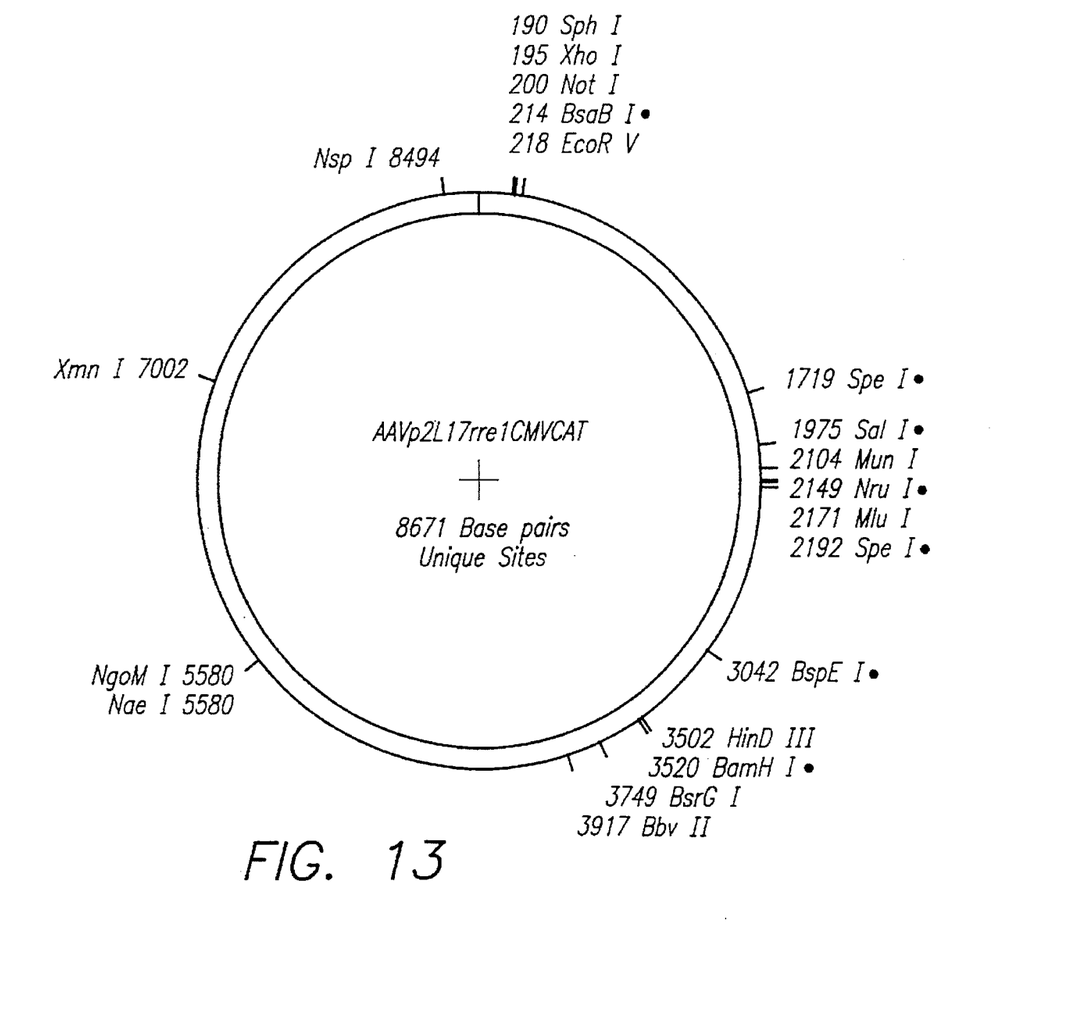
FIG. 13 depicts a circular map of plasmid AAVp2L17rrelCMVCAT.

Subsequently, the SV40 promoter was replaced with the CMV promoter. The resulting plasmid was designated AAVp2L17rreICMVCAT, depicted in FIG. 13.

Example 2

Protocol For Producing AAV/HIV Chimeric Vectors

Twenty (20)/µg of AAV/CAT chimeric plasmid is mixed with 60 µg of the AAV helper plasmid AD8. The DNA mixture is used to transfect $10^7$ HeLa cells which have previously been infected with adenovirus type 5 at an multiplicity of infection (MOI) of 5—10. Approximately 40 hours later maximum cytopathic effect (CPE) is observed. The cells are scraped off the dish and harvested by low speed centrifugation.

The cells are then lysed by three cycles of freeze/thaw. The lysate is then heated to 56° C. to inactivate the adenovirus. The lysate, containing rAAV/CAT particles is then used to transduce $10^5$ HeLa HT4/6C cells (HT4/6C cells express the CD4 receptor which is typically necessary for HIV infection). Subsequently, these cells are infected at an MOI of 1.0 with HIV-1 MN.

Approximately 72 hours later visible CPE occur and the supernatant is collected and used to infect a fresh culture of HeLa HT4 cells. These cells are then analyzed by CAT ELISA 48 hours post-infection. As a negative control, HT4/6C cells infected with supernatant from cells which were infected with HIV-1 without transduction by RAAV are included in the assay.

This protocol uses a recombinant AAV containing the bacterial chloramphenicol acetyl transferase gene (CAT) driven by the cytomegalovirus (CMV) promoter initial experiments used this construct. However, any gene can be substituted for CAT where transduction and subsequent rescue from HIV-1 infected cells is desired. Similarly, any promoter can be used in place of the CMV promoter.

All publications and patent applications cited in this specification are herein incorporated by reference in their entirety for all purposes as if each individual publication or patent application were specifically and individually indicated to be incorporated by reference.

Although the invention has been described with reference to the presently-preferred embodiments, it should be understood that various modifications can be made without departing from the spirit of the invention. Accordingly, the invention is limited only by the claims that follow.

What is claimed is:

1. A vector comprising biologically active nucleic acid sequences from a first and second virus, wherein said nucleic acid sequences of said first virus comprise cis-active AAV nucleic acids for host cell chromosomal integration, said nucleic acid sequences of said second virus comprise a replication defective, rescuable retroviral genome, and wherein said nucleic acid sequences of said second virus also encodes an anti-viral agent operably linked to an expression control sequence.

2. The vector of claim 1, wherein said nucleic acid sequences from said first virus further comprise nucleic acid sequences for nucleic acid replication and encapsidation of the vector.

3. The vector of claim 1, wherein the second virus is an HIV virus.

4. The vector of claim 1, wherein said cis-active nucleic acid sequences are AAV 5' and 3' ITR regions.

5. The vector of claim 1, wherein the second virus is HIV, and wherein the replication defective, rescuable HIV genome encodes a non-functional gene selected from the tat, rev, gag, pol, env, v/f, vpr, nef, and vpu/vpx genes.

6. The vector of claim 1, wherein the second virus is HIV, and wherein the replication defective, rescuable HIV genome does not encode a gene selected from the tat, rev, gag, pol, env, vif, vpr, nef, and vpu/vpx genes.

7. The vector of claim 1, wherein said expression control sequence comprises a constitutive promoter.

8. The vector of claim 1, wherein said expression control sequence comprises an inducible promoter.

9. The vector of claim 1, wherein said expression control sequence comprises an inducible promoter activated in response to viral replication of a replication competent virus corresponding to the replication defective portion of the vector.

10. The vector of claim 1, wherein the anti-viral agent is selected to specifically inhibit the replication of the second virus.

11. The vector of claim 1, wherein said second virus encodes an anti-viral agent selected from the group consisting of an antisense nucleic acid, a ribozyme, a decoy nucleic acid, a transdominant gene and a suicide gene.

12. The vector of claim 1, wherein said second virus encodes an anti viral agent selected from the group consisting of an antisense nucleic acid comprising the HIV TAR or RRE sequence, a decoy nucleic acid molecule comprising the TAR sequence or the RRE sequence, a hammerhead ribozyme, and a hairpin ribozyme.

13. The vector of claim 1, further comprising a nucleic acid encoding a selectable marker operatively linked to an expression control sequence.

14. The vector of claim 1, further comprising a second anti-viral agent operatively linked to an expression control sequence.

15. A mammalian cell transduced with a vector comprising biologically active nucleic acid sequences from a first and second virus, wherein said nucleic acid sequences of said first virus comprise cis-active AAV nucleic acids for host cell chromosomal integration, said nucleic acid sequences of said second virus comprise a replication defective, rescuable retroviral genome, and wherein said nucleic acid sequences of said second virus also encodes an anti-viral agent operably linked to an expression control sequence.

16. The mammalian cell of claim 15 wherein the mammalian cell is a hematopoietic stem cell, fetal cord blood cell, T-lymphocyte or monocyte.

17. A method for inhibiting viral replication in a cell in vitro, comprising transducing the cell with a vector comprising biologically active nucleic acid sequences from a first and second virus, wherein said nucleic acid sequences of said first virus comprise cis-active AAV nucleic acids for host cell chromosomal integration, said nucleic acid sequences of said second virus comprise a replication defective, rescuable retroviral genome, and wherein said nucleic acid sequences of said second virus also encodes an anti-viral agent operably linked to an expression control sequence.

18. The method of claim 17, wherein said transduced cell inhibits viral replication by an HIV virus.

19. The method of claim 17, wherein the cell includes genes necessary for activating an expression control sequence contained within said vector.

20. The method of claim 17, wherein the cell is a hematopoietic stem cell, fetal cord blood cell, T-lymphocyte or monocyte.

21. A method for making anti-viral agents in a cell in vitro, comprising transducing the cell with a vector comprising biologically active nucleic acid sequences from a first and second virus, wherein said nucleic acid sequences of said first virus comprise cis-active nucleic acids encoding viral sequences for host cell chromosomal integration, said nucleic acid sequences of said second virus comprise a replication defective, rescuable viral genome, and wherein said nucleic acid sequences of said second virus encode an anti-viral agent operably linked to an expression control sequence, wherein the cell includes genes necessary for activating said expression control sequence, and culturing the cell under conditions for expression of the anti-viral agent.

* * * * *